(12) United States Patent
Bauhahn et al.

(10) Patent No.: US 7,082,333 B1
(45) Date of Patent: Jul. 25, 2006

(54) PATIENT DIRECTED THERAPY MANAGEMENT

(75) Inventors: Ruth Elinor Bauhahn, Fridley, MN (US); John W. Forsberg, St. Paul, MN (US); Steven James Nelson, Wyoming, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/560,064

(22) Filed: Apr. 27, 2000

(51) Int. Cl.
*A61N 1/34* (2006.01)

(52) U.S. Cl. ............................ 607/60; 607/32; 607/57; 604/891; 600/300

(58) Field of Classification Search ................ 607/30, 607/39–43, 54–60, 65, 98–103, 115–119, 607/154–156, 307; 128/421; 604/65–67, 604/151
See application file for complete search history.

(56) References Cited

U.S. PATENT DOCUMENTS

| | | | |
|---|---|---|---|
| 4,126,139 A | 11/1978 | Walters | |
| 4,236,524 A | 12/1980 | Powell | |
| 4,273,133 A | 6/1981 | Hartlaub | |
| 4,304,238 A | 12/1981 | Fischer | |
| 4,365,633 A | 12/1982 | Loughman | |
| 4,373,527 A | 2/1983 | Fischell | |
| 4,388,927 A | 6/1983 | Schober | |
| 4,390,023 A | 6/1983 | Rise | |
| 4,398,537 A | 8/1983 | Holmbo | |
| 4,407,288 A | 10/1983 | Langer et al. | |
| 4,424,812 A | 1/1984 | Lesnick | |
| 4,459,989 A | 7/1984 | Borkan | |
| 4,467,810 A | 8/1984 | Vollmann | |
| 4,485,818 A | 12/1984 | Leckrone et al. | |
| 4,525,165 A | 6/1985 | Fischell | |
| 4,562,841 A | 1/1986 | Brockway | |
| 4,573,994 A | 3/1986 | Fischell | |
| 4,612,934 A | 9/1986 | Borkan | |
| 4,619,653 A | 10/1986 | Fischell | |
| 4,690,144 A | 9/1987 | Rise | |
| 4,731,051 A | 3/1988 | Fischell | |
| 4,793,353 A | 12/1988 | Borkan | |
| 4,846,180 A * | 7/1989 | Buffet | 607/30 |
| 4,958,632 A | 9/1990 | Duggan | |
| 5,159,926 A | 11/1992 | Jungstroem | |
| 5,231,988 A * | 8/1993 | Wernicke et al. | 128/421 |
| 5,285,781 A | 2/1994 | Brodard | |
| 5,292,341 A | 3/1994 | Snell | |
| 5,318,593 A | 6/1994 | Duggan | |
| 5,360,437 A | 11/1994 | Thompson | |
| 5,370,672 A | 12/1994 | Fowler | |

(Continued)

FOREIGN PATENT DOCUMENTS

EP 0811395 12/1997

(Continued)

OTHER PUBLICATIONS

*Renew Neurostimulation System User's Guide*, by Advanced Neuromodulation Systems, Inc., copyright Mar. 1999.

*Primary Examiner*—Mark Bockelman
(74) *Attorney, Agent, or Firm*—Banner & Witcoff, Ltd.

(57) ABSTRACT

An apparatus and method that allows a patient to access stored preset patient therapy programs, that are resident in a medical device, and to create personalized therapy programs or automatic timing therapy programs from preset therapy programs to accommodate the patient's particular activity. Alternatively, the patient can select and access stored preset patient therapy programs and combine at least two modified or unmodified preset therapy programs to create personalized therapy programs.

18 Claims, 5 Drawing Sheets

U.S. PATENT DOCUMENTS

| | | | | |
|---|---|---|---|---|
| 5,456,691 A | * | 10/1995 | Snell | 607/30 |
| 5,456,692 A | | 10/1995 | Smith | |
| 5,545,186 A | | 8/1996 | Olson | |
| 5,601,617 A | | 2/1997 | Loeb | |
| 5,626,629 A | | 5/1997 | Faltys | |
| 5,681,285 A | * | 10/1997 | Ford et al. | 604/151 |
| 5,697,960 A | | 12/1997 | Molin | |
| 5,716,382 A | | 2/1998 | Snell | |
| 5,755,736 A | | 5/1998 | Gillberg | |
| 5,855,593 A | | 1/1999 | Olson | |
| 5,893,883 A | | 4/1999 | Torgerson et al. | 607/59 |
| 5,938,690 A | | 8/1999 | Law | |
| 5,941,906 A | * | 8/1999 | Barreras, Sr. et al. | 607/66 |
| 5,991,656 A | | 11/1999 | Olson | |
| 6,044,301 A | | 3/2000 | Hartlaub | |
| 6,052,614 A | | 4/2000 | Morris | |
| 6,052,620 A | | 4/2000 | Gillberg | |
| 6,052,624 A | * | 4/2000 | Mann | 607/46 |
| 6,058,326 A | | 5/2000 | Hess | |
| 6,061,596 A | | 5/2000 | Richmond | |
| 6,099,479 A | | 8/2000 | Christopherson | |
| 6,141,581 A | | 10/2000 | Olson | |
| 6,169,924 B1 | | 1/2001 | Meloy | |
| 6,178,350 B1 | | 1/2001 | Olson | |
| 6,181,969 B1 | | 1/2001 | Gord | |
| 6,208,894 B1 | | 3/2001 | Schulman | |
| 6,249,703 B1 | | 6/2001 | Stanton | |
| 6,259,947 B1 | | 7/2001 | Olson | |
| 6,269,270 B1 | * | 7/2001 | Boveja | 607/45 |
| 6,289,247 B1 | | 9/2001 | Faltys | |
| 6,308,102 B1 | | 10/2001 | Sieracki et al. | |
| 6,354,299 B1 | | 3/2002 | Fischell | |
| 6,381,496 B1 | | 4/2002 | Meadows | |
| 6,393,325 B1 | | 5/2002 | Mann | |
| 6,516,227 B1 | | 2/2003 | Meadows | |
| 6,587,724 B1 | | 7/2003 | Mann | |
| 2001/0007950 A1 | | 7/2001 | North et al. | |

FOREIGN PATENT DOCUMENTS

| | | |
|---|---|---|
| EP | 1134003 | 9/2001 |
| EP | 0939661 | 8/2002 |
| GB | 2069844 | 9/1981 |
| WO | WO 84/03218 | 8/1984 |
| WO | WO 95/13112 | 5/1995 |
| WO | WO 96/01665 | 1/1996 |
| WO | WO 96/30081 | 10/1996 |
| WO | WO 97/43002 | 11/1997 |
| WO | WO 01/39831 | 6/2001 |
| WO | W0 01/52935 * | 7/2001 |
| WO | WO 01/93952 | 12/2001 |
| WO | WO 01/93953 | 12/2001 |

* cited by examiner

INS ENVIRONMENT

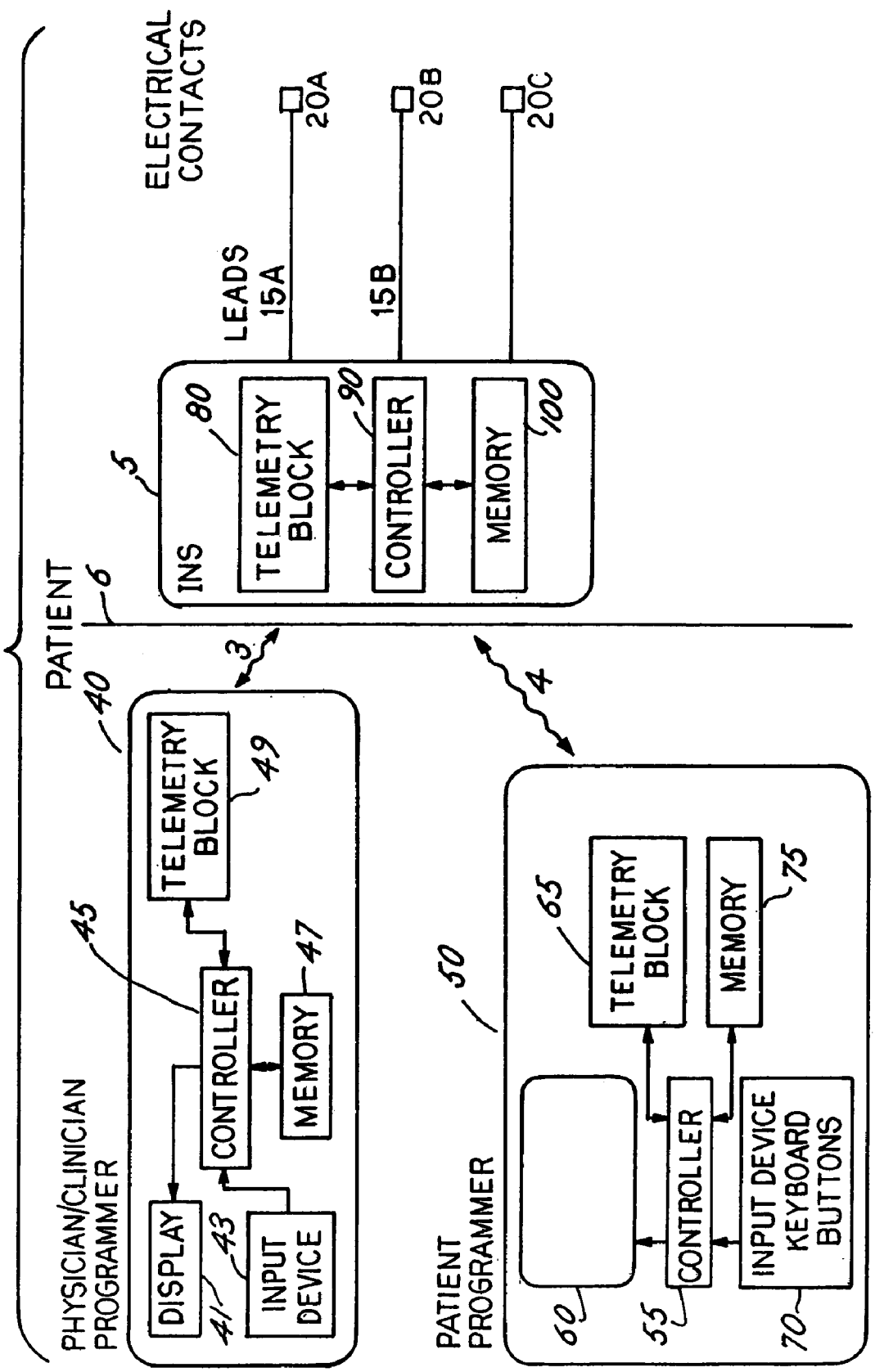

METHOD STEPS

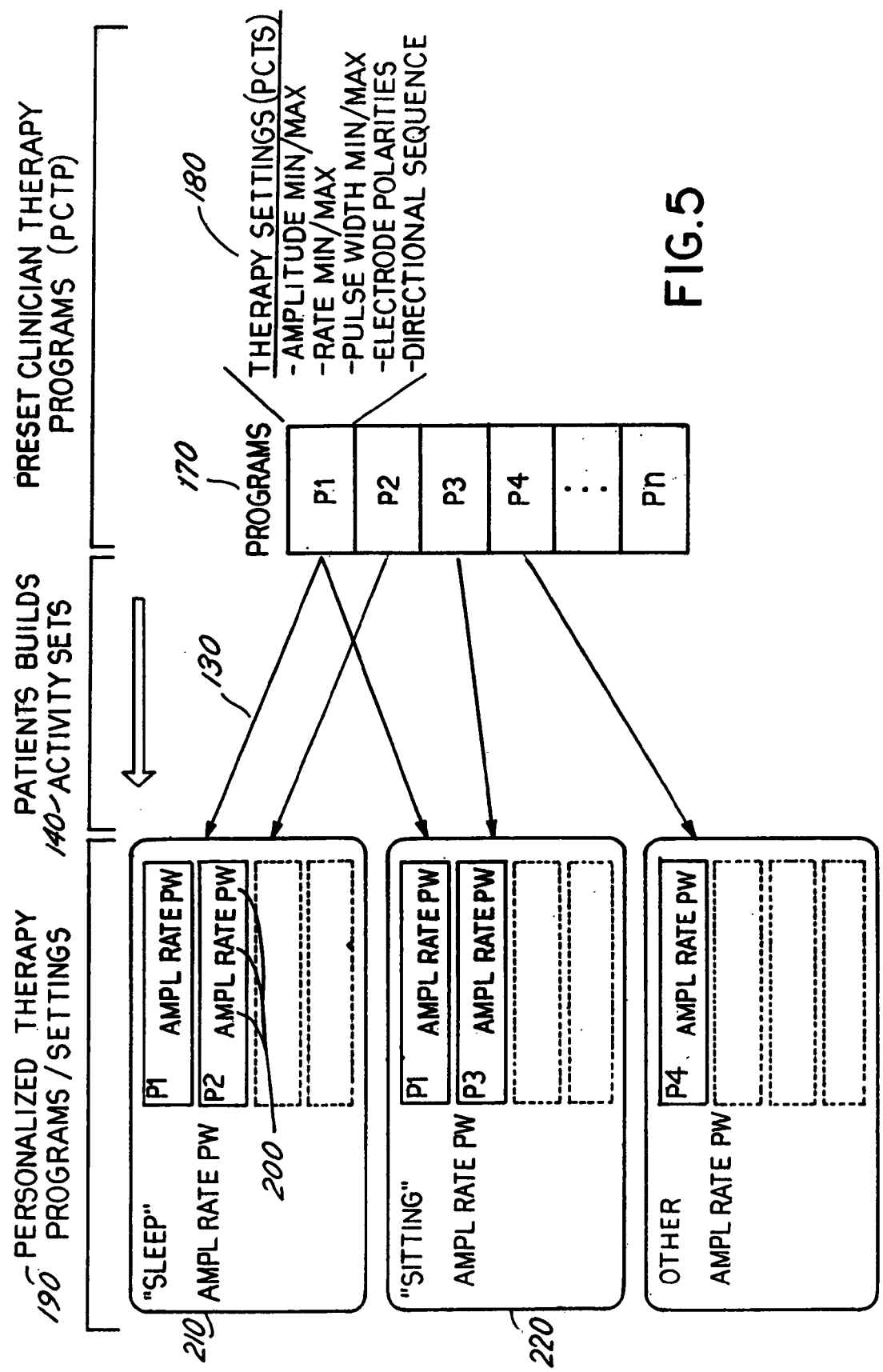

PATIENT DIRECTED THERAPY MANAGEMENT

FIELD OF INVENTION

The present invention relates generally to medical implantable devices. More particularly, the invention relates to an apparatus and method for patient directed therapy management of implantable medical devices used to influence the human body.

BACKGROUND OF THE INVENTION

The medical device industry produces a wide variety of electronic and mechanical devices for treating patient medical conditions. Depending upon the medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life.

Implantable medical devices are commonly used today to treat patients suffering from various ailments. Implantable medical devices can be used to treat any number of conditions such as pain, incontinence, movement disorders such as epilepsy and Parkinson's disease, and sleep apnea. Additionally, use of implantable medical devices appears promising to treat a variety of physiological, psychological, and emotional conditions.

One type of implantable medical device is an Implantable Neuro Stimulator (INS). The INS is implanted at a predetermined location in the patient's body. The INS generates and delivers mild electrical impulses to neurostimulation areas in the body using an electrical lead. The INS electrical stimulation signals at neurostimulation sites or areas influence desired neural tissue, tissue areas, nervous system and organs to treat the ailment of concern. The stimulation sites can also include the spinal cord, brain, body muscles, peripheral nerves or any other site selected by a physician. For example, in the case of pain, electrical impulses may be directed to cover the specific sites where the patient is feeling pain. Neurostimulation can give patients effective pain relief and can reduce or eliminate the need for repeat surgeries and the need for pain medications.

In the case of an INS, the system generally includes an implantable neuro stimulator (INS) (also known as an implantable pulse generator (IPG)), an external physician or clinician programmer, a patient programmer and at least one electrical lead. An INS is typically implanted near the abdomen of the patient, or other stimulation area as required. The lead is a small medical wire with special insulation and contains a set of electrodes (small electrical contacts) through which electrical stimulation is delivered. The INS can be powered by an internal source such as a rechargeable or non-rechargeable battery or by an external source such as a radio frequency transmitter. The INS contains electronics to generate and send precise, electrical pulses to the stimulation area to provide the desired treatment therapy. The clinician programmer is an external device that allows the physician or clinician to create and store preset stimulation therapy to be delivered by the INS. The clinician programmer communicates with the INS using radio waves, for example via telemetry. The patient programmer is an external hand-held device that allows the patient to optimize the stimulation therapy delivered by the INS. The patient programmer also communicates with the INS using radio waves, such as telemetry.

In existing INS devices, a clinician typically creates and stores preset patient therapy programs that are executed by the INS to deliver therapy to the patient. The preset patient therapy programs include specific therapy parameters that are set and created by a clinicians based on industry or clinician preferences, patient feedback, a patient's test results, or a combination of all of the above. The patient therapy programs are then downloaded into INS memory using the clinician programmer. The patient therapy programs then reside in both clinician programmer memory and INS memory. The stored preset patient therapy programs, which include specific therapy parameters, will allow the INS to generate the appropriate electrical stimulation signals for the patient's specific needs. The stored patient therapy programs contain parameters, including for example, electrode settings, signal intensity or strength (amplitude), the signal duration (pulse width), and the signal timing and cycling (pulse frequency or rate).

In addition, the electrodes associated with a medical device, such as an INS, may be arranged in a predetermined physical array or layout configuration at the stimulation site in the patient. In such a case, certain preset therapy parameters in the stored patient therapy programs will allow the INS to generate electrical stimulation signals at the electrodes in a particular directional sequence and physical direction, relative to their physical placement in the patient's body.

At present, patients do not have the ability to select and assemble the preset therapy programs, which were created by the clinician, or to create his/her own personalized therapy programs. A patient can typically access the stored preset clinician therapy programs but cannot create personalized therapy programs himself/herself. A patient must use and live with the preset therapy programs that have been created by the clinician. Moreover, the stimulation areas targeted by the INS's electrical leads on a patient's body are usually situated to alleviate or address pain or discomfort due to one body position or activity, e.g., sitting compared to walking, jogging or running. As a result, the combination of specifically situated stimulation areas and unchangeable clinician created preset therapy programs can lead to discomfort when a patient engages in activities that were not accounted for or foreseen by the clinician. The inability to modify the stored therapy programs can thus limit the activities that a patient may wish to engage in.

For the foregoing reasons there is a need for an apparatus and method that will allow patients to access stored preset clinician therapy programs so that the patient can create new personalized therapy programs that will enable the patient to participate in a variety of activities without undue discomfort or the need to visit a clinician for additional preset therapy programs.

It is an objective of the present invention to provide an apparatus and method to give patients the ability to assemble, label and store their own personalized therapy programs, on demand, from among the preset clinician therapy programs that are resident in INS memory.

It is an objective of the present invention to provide an apparatus and method to give patients more control to create personalized therapy programs and settings to fit their unique lifestyles thereby increasing patient satisfaction.

SUMMARY OF THE INVENTION

The present invention provides an apparatus and method that allows a patient to select and access stored patient therapy programs, that are resident in the INS device, and modify the stored therapy programs to accommodate his/her particular lifestyle, thereby creating and storing personalized therapy programs. The patient can select and access stored patient therapy programs and combine in an unmodified manner at least two of the accessed therapy programs to create personalized therapy programs. The present invention also gives the patient the ability to select and access stored patient therapy programs, to modify the accessed preset therapy programs and then combine the modified preset therapy programs to create personalized therapy programs.

In accordance with the present invention, there is provided a method for patient directed therapy management in an implantable neuro stimulator (INS). The method comprised of: storing preset clinician therapy programs with preset therapy settings in an INS device; accessing the preset clinician therapy programs by the patient, via telemetry communication between the INS device and a patient programmer; modifying at least one of the accessed preset clinician therapy programs on a patient programmer to create at least one personalized therapy program with personalized therapy settings; and storing the personalized therapy program in the INS device for subsequent use by the patient. A patient can then select from the clinician preset therapy programs or from the newly created and stored personalized therapy settings in accordance with the activity and/or preference of the patient.

In accordance with the present invention, there is provided a system for patient directed therapy management that allows a patient to select and access stored patient therapy programs that are resident in the INS device and to modify the stored therapy programs to create and store personalized therapy programs that accommodate the patient's particular lifestyle. The system apparatus is comprised of an implantable neuro stimulator (INS) with memory able to receive, store and execute preset patient therapy programs; a physician or clinician programmer for creating and storing preset patient therapy programs; a patient programmer with a display screen for creating and storing personalized therapy programs; and electrical lead electrodes for delivering therapy signals. In the system for patient directed therapy management, the clinician programmer, the patient programmer and the INS communicate using radio waves, for example, via telemetry.

In other embodiments, the apparatus and method for patient directed therapy management of the present invention can be used with any number of implantable systems requiring the use of preset therapy programs, including, but not limited to, pacemakers, defibrillators, cochlear implants, implantable diagnostic devices for detecting bodily conditions of certain organs, like the brain or the heart, and drug delivery systems having an implantable pump.

BRIEF DESCRIPTION OF THE DRAWINGS

FIG. 3 is a schematic block diagram of an INS in accordance with a preferred embodiment of the present invention.

FIG. 5 is a block diagram representation showing in more detail certain steps of FIG. 4 for creating personalized therapy programs.

DESCRIPTION OF THE PREFERRED EMBODIMENTS

The present invention is an apparatus and method that allows a patient to select and access stored preset clinician patient therapy programs from INS memory and to modify the preset clinician therapy programs to create and store personalized therapy programs through the use of a patient programmer. The present invention gives the patient the ability to configure personalized therapy programs that accommodate the patient's particular needs, lifestyle, and desires from combined and/or modified stored preset clinician therapy programs.

Figure 1:
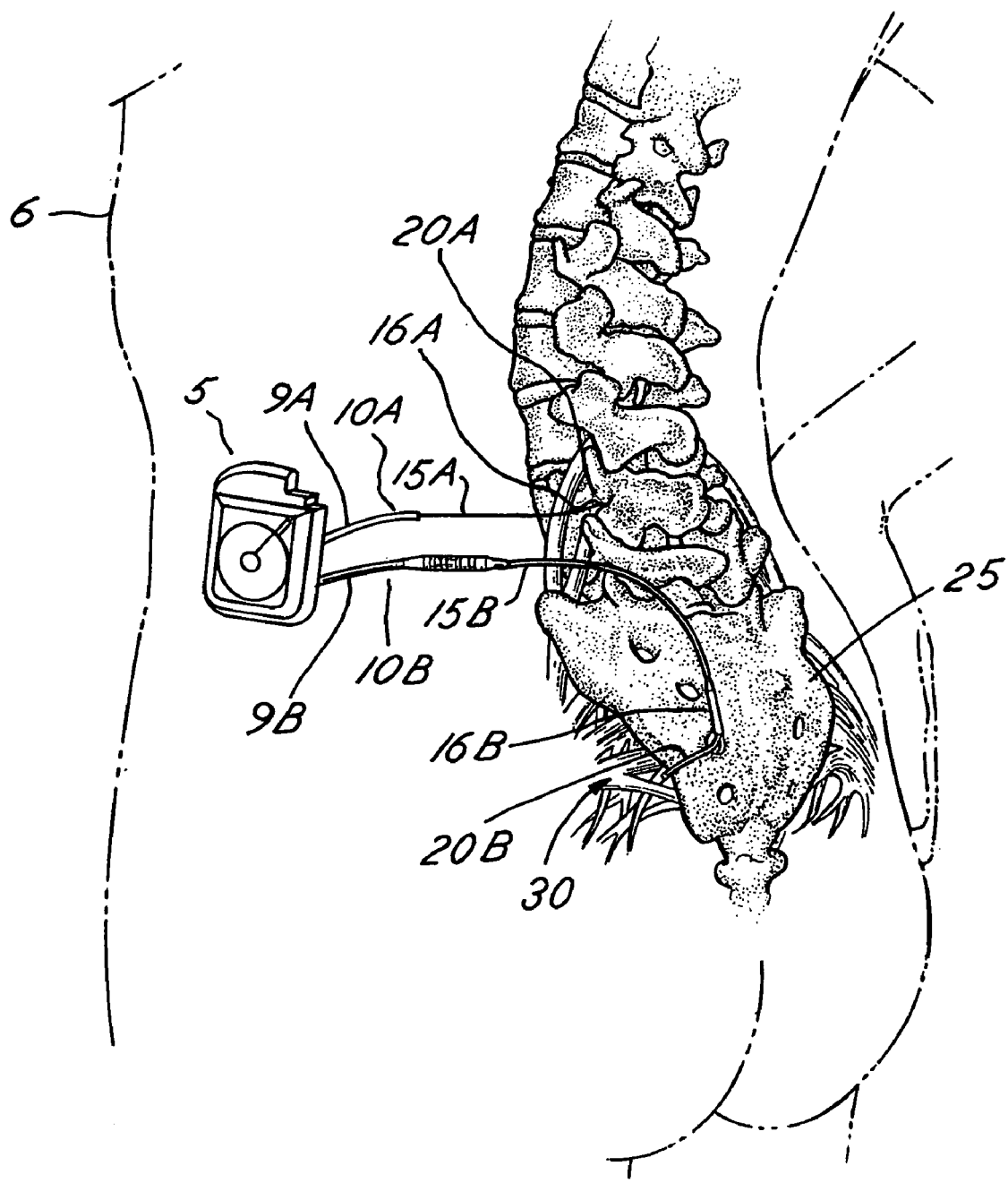
FIG. 1 illustrates an implantable medical device as could be implanted in a human body to deliver stimulation therapy.

FIG. 1 shows a general environment of an Implantable Neuro Stimulator (INS) 5 medical device in a patient 6 including leads 15A and 15B, and lead extensions 10A and 10B. The INS 5 is preferably a modified implantable pulse generator that will be available from Medtronic, Inc. with provisions for multiple pulses occurring either simultaneously or with one pulse shifted in time with respect to the other, and having independently varying amplitudes, pulse widths and directional sequence. The INS 5 contains a power source and electronics to send precise, electrical pulses to the spinal cord, brain, or neural tissue to provide the desired treatment therapy. The INS 5 can be powered by an internal source such as a rechargeable or non-rechargeable battery or by an external source such as a radio frequency transmitter. In a preferred embodiment of the present invention, the INS 5 provides electrical stimulation by way of pulses, however other forms of stimulation may be used such as continuous electrical stimulation.

The INS 5 can use one or more leads 15A and 15B and extensions 10A and 10B for delivering therapy. The leads 15A and 15B, which are surgically implanted, are comprised of one or more insulated electrical conductors with a connector on the proximal end 9A and 9B and electrical contacts or electrodes 20A and 20B on the distal end 16A and 16B. A lead 15A and 15B is a small medical wire with special insulation. Those skilled in the art will appreciate that any variety of leads may be used to practice the present invention.

As shown in FIG. 1, the leads 15A and 15B are implanted and positioned to stimulate a specific site or area. Alternatively, the leads 15A and 15B may be positioned along a peripheral nerve, adjacent neural tissue, positioned to stimulate muscle tissue or other stimulation site chosen by a clinician. The leads 15A and 15B contain one or more electrodes (small electrical contacts) through which electrical stimulation is delivered from the INS 5 to the targeted neural tissue. The electrodes 20A and 20B may be arranged in a predetermined physical layout. For example, where there is more than one electrode 20A and 20B, the electrodes may be arranged in a linear array, in multiple linear arrays, or in a particular geometric array such as a triangle, square, rectangle, circle, etc. In addition, the INS 5 may deliver stimulation therapy signals via the electrodes in a predetermined directional sequence based on the electrode's physical layout in the stimulation area.

Figure 2A:
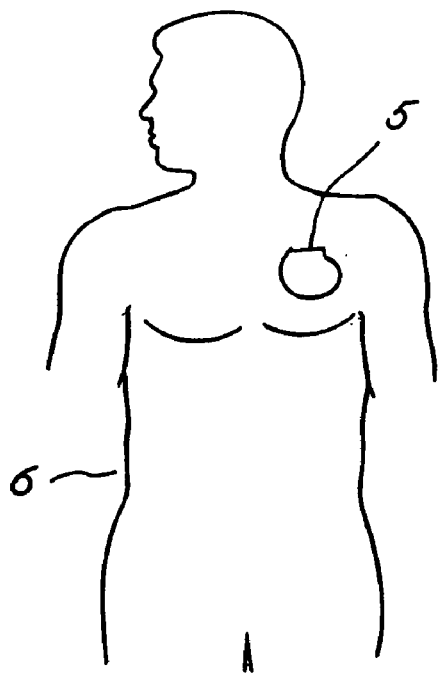
FIGS. 2A–D illustrate locations where the implantable medical device can be implanted in the human body other than the location shown in FIG. 1.
Figure 2B:
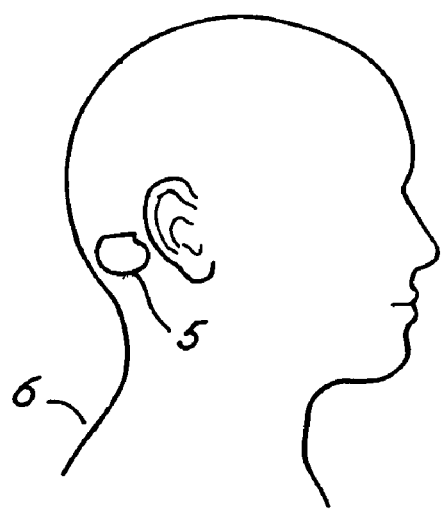
Figure 2C:
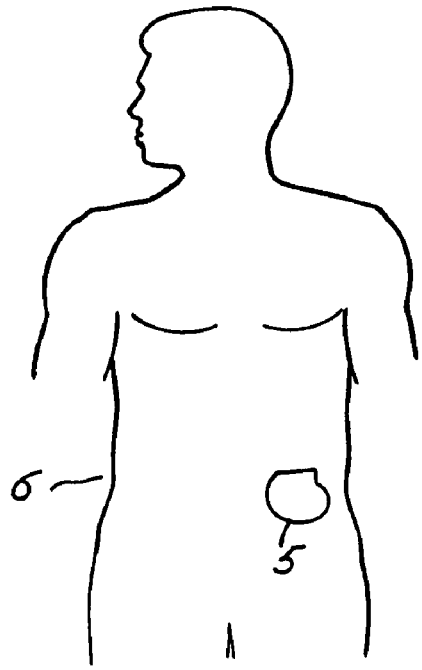
Figure 2D:
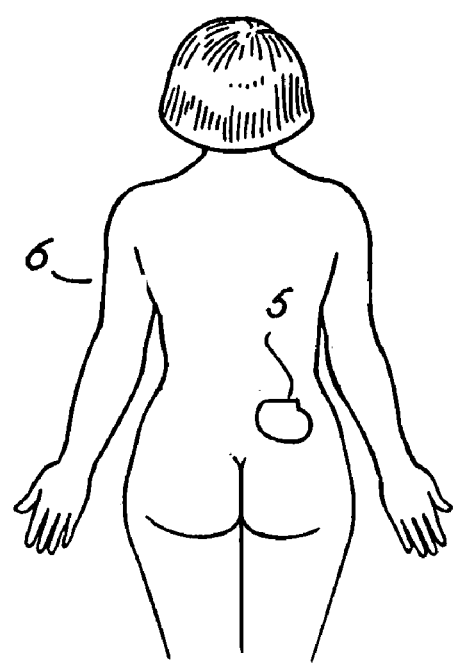

FIGS. 2A–D generally illustrate locations where the INS can be implanted in the human body other than the location shown in FIG. 1, i.e., within the lower left abdominal region of the patient 6 illustrated in FIG. 2C. Other preferred embodiments for the placement of INS 5 within a human patient are further shown in FIGS. 2A, 2B, and 2D. As shown in FIG. 2A, the INS 5 can be implanted in a pectoral region of the patient. As shown in FIG. 2B, the INS 5 can be implanted in a region behind the ear of a patient 6, and more specifically in the mastoid region. As shown in FIG. 2D, the INS 5 can be placed in the lower back or upper buttock region of the patient 6.

FIG. 3 generally depicts system components of a preferred embodiment of the present invention that allows a patient to select and access preset patient therapy programs from the INS 5 in preparation for creating personalized therapy programs. The apparatus included are an INS 5 with corresponding leads 15A and 15B, a physician or clinician programmer 40 and a patient programmer 50. In the system apparatus, the clinician programmer 40, the patient programmer 50 and the INS 5 communicate using radio waves, for example via telemetry 3 and 4.

In a preferred embodiment, the clinician programmer 40 is used by the clinician to create preset clinician therapy programs for a particular patient. The clinician can also modify the preset therapy stored in the INS memory 100, troubleshoot the INS 5, and periodically communicate with the INS 5 to manage the patient therapy and collect INS data. The clinician can create the preset clinician therapy programs via the clinician programmer input medium or device 43, for example a keyboard, or any other input component recognized by the clinician programmer controller 45.

The preset clinician therapy programs include specific therapy parameters and electrode settings that can be based on industry or clinician preferences, patient feedback, patient test results, or a combination of all. The clinician can simultaneously view the preset programs as he/she is creating them on the graphical display screen 41. Upon completion of the preset therapy programs, the clinician programmer controller 45 will execute the clinician's instruction to save the preset programs. The clinician programmer controller 45 will save the preset programs in its memory 47 and download a copy to the INS memory 100 via telemetry 3. In a preferred embodiment, only a copy of the preset clinician therapy programs are downloaded to the INS device 5. A master copy of the preset clinician therapy programs remains with the clinician in the clinician programmer memory 47. The stored patient therapy programs (both preset and personalized) in the INS device 5 will allow the INS device 5 to generate the electrical stimulation signals for the patient's specific needs. The therapy programs will control such electrode settings as signal amplitude, rate, pulse width, and directional sequence.

In an embodiment of the present invention, as will be discussed below, a patient can access the preset clinician therapy programs (PCTP) stored in the INS via the patient programmer 50. The patient programmer 50 can comprise a graphical display screen 60, an input medium or device 70, a patient program controller 55, memory 75 and a telemetry block 65. Having accessed a PCTP, the patient can then create at least one personalized therapy program from the accessed PCTP. The patient can then store the new personalized therapy program in the INS 5 via the patient programmer 50 input device 70.

For example, in the embodiment shown in FIG. 3, a patient could step through the following to create and store at least one personalized therapy program 190 (discussed with reference to FIG. 5). First, a patient would turn the patient programmer 500N and start the process in a first Start Screen. Second, the patient would select a Review function and interrogate the INS 5 via the input device 70. The patient would then select a Select Menu function that brings up a Selection Screen on the graphical display screen 60. The Selection screen would display a Menu indicating the various preset clinician therapy programs (PCTP) 170 (discussed in more detail with reference to FIG. 5) that are resident in the INS memory 100. The patient could then scroll through the Menu (on the graphical display screen 60) and select the particular PCTP 170 that he/she wishes to access in order to create at least one personalized therapy program. Having accessed a PCTP 170, the patient can then review and modify the preset clinician therapy settings (PCTS) 180 (discussed in more detail with reference to FIG. 5) that correspond to the accessed PCTP 170. The patient may then select and optimize a PCTS 180 as necessary or desired by use of the graphical display screen 60 and the input device 70.

The patient can then make changes as desired for any of the other remaining PCTS 180 of the accessed PCTP 170 as necessary to create a personalized therapy program 190. Once the patient has created a personalized therapy program 190, a Save function can be selected. A Save screen could then be displayed where the user would create a label for the created personalized therapy program. For example, the user could label the just created personalized therapy program 190 a "Sleep" program. The patient would then select a Store function and a Store screen would be displayed. The patient would then, via the input medium key for example, store the personalized therapy program in the INS memory 100. The patient programmer controller 55 will execute the patient's instruction to save the new programs. The patient programmer can save the new programs in its memory 75 and download a copy to the INS memory 100. The new programs will be transmitted via telemetry 4 to the INS 5 where the will be saved in INS memory 100. The patient could repeat the above steps to create other personalized therapy programs 190, for example programs such as "Running", "Eating", "Sitting", "Exercising" and others.

The steps just discussed in creating personalized therapy programs 190 involve patient interaction with the graphical display screen 60 and input device 70 of the patient programmer 50 and can be an embodiment of a personalized therapy algorithm. Those of skill in the art will readily recognize that the patient's commands and instructions are being carried out by the patient programmer controller 55. The controller 55 will then transmit instructions via its telemetry block 65 to the INS 5.

In other embodiments, the patient could create personalized therapy programs as combinations of unmodified preset programs, or combinations of both modified and unmodified preset clinician therapy programs (PCTS) via a similar process.

Having created and stored personalized therapy programs, the patient can then access, modify is necessary and execute at least one personalized therapy programs via the patient programmer 50. A patient can access the personalized therapy programs via the patient programmer 50. Having accessed the personalized therapy settings, the patient can then optimize and execute the personalized therapy programs to receive therapy.

For example, a patient could step through the following to access and execute at least one personalized therapy program 190. First, a patient would turn the patient programmer 50 ON and start the process in a first Start Screen. Second, the patient would select a Review function and interrogate the INS 5 via the input device 70. The patient would then select a Select Menu function that brings up a Selection Screen on the graphical display screen 60. The Selection screen would display a Menu indicating the various preset clinician therapy programs (PCTP) 170 and personalized therapy programs 190 that are resident in the INS memory 100. The patient could then scroll through the Menu and select the particular personalized therapy program that he/she wishes to view access in order to execute for therapy via the INS. Having accessed a personalized therapy program, the patient may then select a personalized therapy program and optimize as necessary or desired by use of the graphical display screen 60 and the input device 70.

If no optimization of the accessed personalized therapy program 190 is done, then an Execute function is selected via the input device 70. An Execute Personalized Therapy Screen will be displayed on the patient programmer display 60. The patient will then select execution of the accessed personalized therapy program 190, for example via the input device 70.

If the patient does optimize the accessed personalized therapy program 190, the Save function would be selected. A Save screen would then be displayed where the user would select a Store function. In a Store screen the patient would then, via the input medium key for example, store the optimized personalized therapy program 190 in the INS device 5. The Execute function is then selected via the input device 70. An Execute Personalized Therapy Screen will be displayed where the patient will select execution of the accessed personalized therapy program 190, for example via the input device 70. Again, the patient programmer controller 55 will carry out the patient's instruction to execute, and optimize if desired, the personalized therapy program 190.

In another embodiment, a patient will be able to execute an automatic timing algorithm on the patient programmer controller 55. The execution of the timing algorithm is similar to the personalized therapy algorithm just discussed. However, while the personalized therapy algorithm allows the patient to create personalized therapy programs and download them to the INS memory 100, the timing algorithm will allow the patient to create personalized automatic sequencing programs where personalized therapy programs, preset therapy programs, or a combination of both will automatically be executed by the INS 5. The patient will store the personalized automatic sequencing programs in the INS memory for subsequent execution at predetermined times for predetermined periods of time. For example, the patient could create a personalized automatic sequencing program that automatically executes certain predetermined therapy programs every morning at 6:30 AM for 1.5 hours.

The INS 5 also uses telemetry 3 and 4 to communicate with the clinician programmer 40 or patient programmer 50. The INS 5 comprises an INS controller 90, memory 100 and a telemetry block 80. The INS controller 90 processes instructions received at the telemetry block 80. In the preferred embodiment, the INS controller 90 will either download or upload data to or from the INS memory 100 depending on the instructions received at the telemetry block 80. The INS memory 100 includes memory sufficient for operation of the INS 5 and storage of all therapy programs. Those skilled in the art will appreciate that the INS memory 100 includes memory such as volatile Random Access Memory (RAM) such as Static RAM, nonvolatile Read Only Memory (ROM), and Electrically Erasable Programmable Read Only Memory (EEPROM) such as Flash EEPROM, as well as other suitable INS memory 100. Once the personalized therapy programs have been downloaded, upon instructions by the patient programmer 50, the INS controller 90 will be able to execute both the preset clinician therapy programs and the personalized therapy programs.

Figure 4:
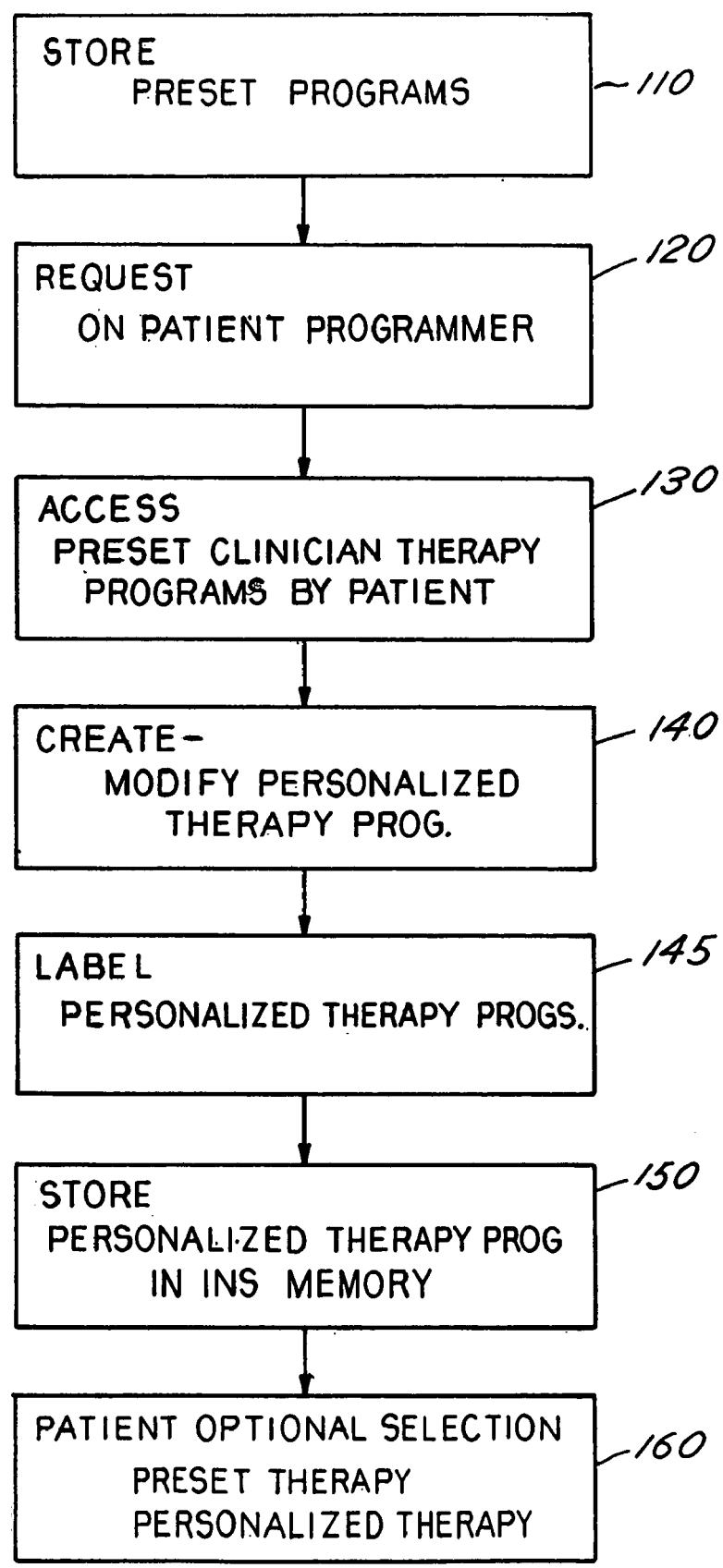
FIG. 4 depicts a block diagram that shows a preferred method of the present invention to create personalized therapy programs.

FIG. 4 shows a block diagram depicting a preferred method of the present invention for a patient to create personalized therapy programs for storage in an INS 5. In a first step 110, preset clinician therapy programs with electrode therapy settings are stored in the INS memory 100.

In a second step 120, the patient interactively (as discussed previously with respect to FIG. 3) enters a request, via the patient programmer input medium 70 and graphical display screen 60.

In a third step 130, the preset clinician therapy programs have been accessed and are displayed on the patient programmer graphical display screen 60 and stored in the patient programmer memory 75.

In step four 140, the patient creates personalized therapy programs, with personalized therapy settings (discussed in FIG. 5), by modifying the accessed preset clinician therapy programs. The personalized therapy programs are created through interaction (as discussed previously with respect to FIG. 3) with the patient programmer 50, via the patient programmer input device 70 and graphical display screen 60.

In step five 145, the patient will label the created personalized therapy programs in preparation for saving or storing.

In step six 150, the patient stores the new personalized therapy programs with personalized therapy settings in the INS memory 100, under the particular labels chosen by the patient. Storing is accomplished through interactive manipulation (as discussed previously with respect to FIG. 3) of the patient programmer 50 by the patient. Once the patient requests that the new programs be stored, the patient programmer 50 will download the newly created personalized therapy programs to the INS memory 100, via telemetry communication 4. The INS device 5 will now be able to execute the new stored personalized therapy programs.

In step seven 160, the patient can execute select either a preset clinician therapy program or a personalized therapy program in accordance with the patient's activity and/or preference.

FIG. 5 depicts a block diagram representation showing, in more detail, steps executed by the patient to create personalized therapy programs from preset therapy programs already present in the INS 5. As discussed previously, physician defined programs or preset clinician therapy programs (PCTP) 170 are created on a clinician programmer 40 (shown in FIG. 3) and downloaded via telemetry 3 and stored (shown in FIG. 3) in the INS memory 100. At the patient's discretion, a patient can access the PCTPs via a patient programmer 70. The patient can then build or create personalized activity sets or personalized therapy programs 190.

Typically, there is more than one PCTP 170 downloaded and stored in the INS memory 100. FIG. 5 shows that there are N number of PCTPs 170 stored in INS memory 100 each labeled P1, P2, P3, P4, . . . PN. Further, each PCTP 170, includes particular Preset Clinician Therapy Setting (PCTS) 180 such as stimulation amplitude, rate, pulse width, electrode polarities, and directional sequence. As result, each of the PCTPs 170 labeled P1, P2, P3, P4, . . . PN have their own corresponding set of PCTS 180 (Amplitude1, Rate1, PW1; Amplitude2, Rate2, PW2; Amplitude3, Rate3, PW3; . . . AmplitudeN, RateN, PWN). The patient will in turn create his/her own personalized therapy programs 190 with corresponding personalized therapy settings 200 from the available N number of PCTPs 170 stored in the INS memory 100.

The patient, however, has flexibility in creating his/her personalized therapy programs 190 and settings 200. In a first case, the patient can access a single PCTP 170 (e.g., P1) and build or create a personalized therapy program 170 with corresponding personalized settings 200 by adjusting or modifying the PCTS 180 (i.e., Amplitude1, Rate1, PW1) of that single accessed PCTP 170. Having created a personalized therapy program 190, the patient will then define or label the new personalized therapy program 190.

Alternatively, in a second case shown in FIG. 5, the patient can access any two PCTPs 170 (e.g., P1 and P2) to build or create a new personalized therapy program 190. In this case, the patient could decide to make no modifications to the PCTS 180 (i.e. Amplitude1, Rate1, PW1 and Amplitude2, Rate2, PW2) of the chosen PCTPs 170 and simply have this personalized therapy program 190 be a combination of the two chosen PCTPs 170 with their PCTS 180 unmodified. This case is shown by the personalized therapy program 190 labeled "Sleep" 210.

In a third case, as shown in FIG. 5, the patient can access any two PCTPs 170 (e.g., P1 and P3) to build or create a new personalized therapy program 170. In this case, the patient could decide to make changes to the PCTS 180 (i.e., Amplitude1, Rate1, PW1 and Amplitude3, Rate3, PW3) of one or both of the chosen PCTPs 170. The result would be a personalized therapy program 190 that is a combination of the two chosen PCTPs 170 with one or both of the PCTS 180 modified, for example as shown by the personalized therapy program 190 labeled "Sitting" 220. The patient can create any desired number of personalized therapy programs 190 through repetition of the steps discussed with respect to FIGS. 3–5.

Additionally, it will be readily appreciated by those skilled in the art that the patient could actually access any number of PCTPs 170 (i.e., P1, P2, P3 up to PN) or all the PCTPs 170 to build or create a new personalized therapy program 170. In such a case, the patient could make changes to any number or all of the PCTS 180 (i.e., the Amplitude, Rate, PW) of any one or all of the chosen PCTPs 170. The result would then be a personalized therapy program 190 that is a combination of the chosen PCTPs 170 with some or all PCTS 180 modified.

In the preferred embodiments of the present invention, discussed with reference to FIGS. 3–5, patient was able to access and create personalized therapy programs 170 through the interactive operation of a patient programmer 70. However, those skilled in the art will readily recognize that a patient programmer 70 is only one of many component that can be used for this function. For example, a computing device could also be used as the medium to create and store personalized therapy programs 170.

It will also be apparent to those of skill in the art that the arrangement and configuration of components of the present invention is only the preferred embodiment of the present invention. For example, those skilled in the art will readily recognized that the present invention can also be used with an External Neuro Stimulator (not shown), with stimulation leads that are implanted into a patient percutaneously, a physician programmer, and a patient programmer. The ENS functions similarly to the INS but is not designed for implantation.

In other embodiments, the apparatus and method for patient directed therapy management of the present invention can be used with any number of implantable systems requiring the use of preset therapy programs, including, but not limited to, pacemakers, defibrillators, and cochlear implants, implantable diagnostic devices for detecting bodily conditions of certain organs, like the brain or the heart, and drug delivery systems having an implantable pump.

Those skilled in that art will recognize that the preferred embodiments may be altered or amended without departing from the true spirit and scope of the invention. Thus, while various alteration and permutations are possible, the invention is limited only by the following claims and equivalents.

We claim:

1. In a patient programmer, a method for patient-directed therapy management for a medical device comprised of:
   accessing by a patient with the patient programmer via telemetry at least two preset clinician therapy programs stored in the medical device;
   creating by the patient at least one personalized therapy program from the accessed preset clinician therapy programs, the at least one personalized therapy program based on patient activity;
   labeling the personalized therapy program according to said patient activity
   storing the personalized therapy program in the patient programmer;
   transmitting the personalized therapy program to the medical device;
   storing the personalized therapy program in the medical device; and
   executing at least one personalized therapy program.

2. The method for patient directed therapy management of claim 1 wherein the personalized therapy program comprises at least one personalized therapy setting.

3. The method for patient directed therapy management of claim 2 wherein the personalized therapy settings are comprise of at least one of an amplitude, a rate, a pulse width, a pulse frequency, electrode polarities, or a directional sequence.

4. The method for patient directed therapy management of claim 2 wherein the patient programmer executes a personalized therapy algorithm.

5. The method for patient directed therapy management of claim 2 wherein the patient programmer executes a timing algorithm.

6. The method for patient directed therapy management of claim 2 wherein the medical device is an implantable neuro stimulator.

7. The method for patient directed therapy management claim 2 wherein the medical device is an external neuro stimulator.

8. In a patient programmer, a method for patient-directed therapy management for a medical device comprised of:
   accessing by a patient with the patient programmer via telemetry at least two preset clinician therapy programs stored in the medical device;
   creating by the patient at least one personalized therapy program from the accessed preset clinician therapy programs, the at least one personalized therapy program based on patient activity, the personalized therapy program comprises at least one personalized therapy setting;
   labeling the personalized therapy program according to said patient activity
   storing the personalized therapy program in the medical device;
   executing at least one personalized therapy program; and
   wherein the medical device is selected from the group consisting of a pacemaker, a defibrillator, a cochlear implant, an implantable diagnostic device, and an implantable pump.

9. In a patient programmer, a method for patient-directed therapy management for a medical device, the method comprising the steps of:
- communicating with the medical device using telemetry through a telemetry block of the patient programmer;
- accessing by a patient with the patient programmer via telemetry at least two preset clinician therapy programs stored in the medical device;
- creating by the patient at least one personalized therapy program from the accessed preset clinician therapy programs, the at least one personalized therapy program based on patient activity, the personalized therapy program comprising at least one personalized therapy setting;
- labeling the personalized therapy program according to said patient activity
- communicating the personalized therapy program to the medical device; and
- storing the personalized therapy program in the medical device.

10. The method for patient directed therapy management of claim 9 wherein the at least one personalized therapy setting comprises an amplitude.

11. The method for patient directed therapy management of claim 9 wherein the at least one personalized therapy setting comprises a pulse rate.

12. The method for patient directed therapy management of claim 9 wherein the at least one personalized therapy setting comprises pulse width.

13. The method for patient directed therapy management of claim 9 wherein the at least one personalized therapy setting comprises a pulse frequency.

14. The method for patient directed therapy management of claim 9 wherein the at least one personalized therapy setting comprises electrode polarities.

15. The method for patient directed therapy management of claim 9 wherein the at least one personalized therapy setting comprises a directional sequence.

16. The method for patient directed therapy management of claim 9 wherein the medical device is an implantable neuro stimulator.

17. The method for patient directed therapy management claim 9 wherein the medical device is an external neuro stimulator.

18. The method for patient directed therapy management of claim 9 wherein the medical device is selected from the group consisting of a pacemaker, a defibrillator, a cochlear implant, an implantable diagnostic device, and an implantable pump.

* * * * *